(12) United States Patent
Iwata

(10) Patent No.: US 7,117,723 B2
(45) Date of Patent: Oct. 10, 2006

(54) FRACTIONATING APPARATUS

(75) Inventor: Yosuke Iwata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/879,968

(22) Filed: Jun. 29, 2004

(65) Prior Publication Data

US 2005/0072218 A1   Apr. 7, 2005

(30) Foreign Application Priority Data

Sep. 24, 2003   (JP) .............................. 2003-330841

(51) Int. Cl.
*B65B 3/30* (2006.01)
(52) U.S. Cl. .................................... 73/61.55
(58) Field of Classification Search ...................... None
See application file for complete search history.

(56) References Cited

U.S. PATENT DOCUMENTS 5,220,172 A * 6/1993 Berthold et al. ......... 250/461.1
6,355,164 B1   3/2002 Wendell et al.
6,672,344 B1 * 1/2004 Stokes et al. ................ 141/234

FOREIGN PATENT DOCUMENTS

| JP | 07-181164 | 7/1995 |
| JP | 2002-055040 | 2/2002 |
| JP | 2002-156382 | 5/2002 |

* cited by examiner

*Primary Examiner*—Daniel S. Larkin
*Assistant Examiner*—Paul M. West
(74) *Attorney, Agent, or Firm*—Rankin, Hill, Porter & Clark LLP

(57) ABSTRACT

A proximity sensor for measuring a distance between a probe and a sample plate is provided a sideway of the probe. The sample plate is mounted on a stage and moved vertically and horizontally. The stage is connected to a control unit for controlling the movement of the stage. The control unit makes a feedback control for the stage so that the measured value of the proximity sensor may be set to a preset value. When dropping a liquid droplet from the probe, the sample plate is moved upwards to shorten the distance between the probe and the sample plate and contact the liquid droplet with the sample plate, whereby the solution is fractionated.

9 Claims, 2 Drawing Sheets

FRACTIONATING APPARATUS

BACKGROUND OF THE INVENTION

1. Field of the Invention

The present invention relates to a fractionating apparatus for fractionating a liquid containing sample constituents onto a sample plate by dropping the liquid from a distal end of a probe.

2. Description of the Related Art

In the related art, when an effluent solution from a liquid chromatography is automatically dropped from a distal end of a probe onto a sample plate for MALDI-TOF (Matrix assisted laser desorption ionisation time of flight) or FT-IR (Fourier Transform Infrared Spectroscopy), the sample plate is moved closer to the effluent solution appearing from the distal end of the probe, because the amount of liquid droplet to be dropped is as small as about 1 μL, the sample plate is contacted with the liquid droplet, and the effluent solution is fractionated onto the sample plate.

In the related-art apparatus, using a method for fractionating the liquid by moving the sample plate closer to the liquid droplet, the sample plate and the liquid droplet are contacted at one point to fractionate the liquid successfully, but the liquid droplet and the sample plate are not contacted or a distal end of the probe contacts the sample plate at another point on the sample plate, resulting in a failure of hurting the surface of the sample plate, because the sample plate is not necessarily supported completely horizontally. In the MALDI-TOF analysis, because an electric field is applied to the sample plate at the time of analysis, the spreading of electric field is not uniform, if the sample plate is hurt, causing the analysis precision to be worse.

SUMMARY OF THE INVENTION

Thus, it is an object of this invention to provide a fractionating apparatus in which the distance between the sample plate and the distal end of the probe is kept constant at any time in dropping a liquid droplet on the sample plate.

This invention provides a fractionating apparatus comprising a probe for dropping a liquid droplet from its distal end, a plate for collecting the liquid droplet dropped from the probe, a support mechanism for moving the plate or the probe at least vertically, a distance measuring unit for measuring a distance from a distal end portion of the probe and the plate, and a control unit for controlling a movement of the support mechanism so that the distance between the distal end of the probe and the plate is equal to a preset distance, based on a measured result of the distance measuring unit when dropping the liquid droplet from the probe.

It is preferable that the control unit can variably set the distance between the distal end of the probe and the plate when dropping the liquid droplet from the probe.

The probe may be connected to a distal end of a capillary column through which an effluent solution from a liquid chromatography is fed.

The plate may be a sample plate for MALDI-TOF, or a sample plate for FT-IR.

Since the distance measuring unit for measuring the distance between the distal end portion of the probe and the plate is provided to set the measured distance to the preset distance, it is possible to prevent occurrence of a situation where the distance between the probe and the sample plate is too large or zero.

If the probe is connected to the capillary column of the liquid chromatography, the effluent solution containing the sample constituents separated by the liquid chromatography can be fractionated and collected.

DETAILED DESCRIPTION OF THE INVENTION

One embodiment of the present invention will be described below.

Figure 1:
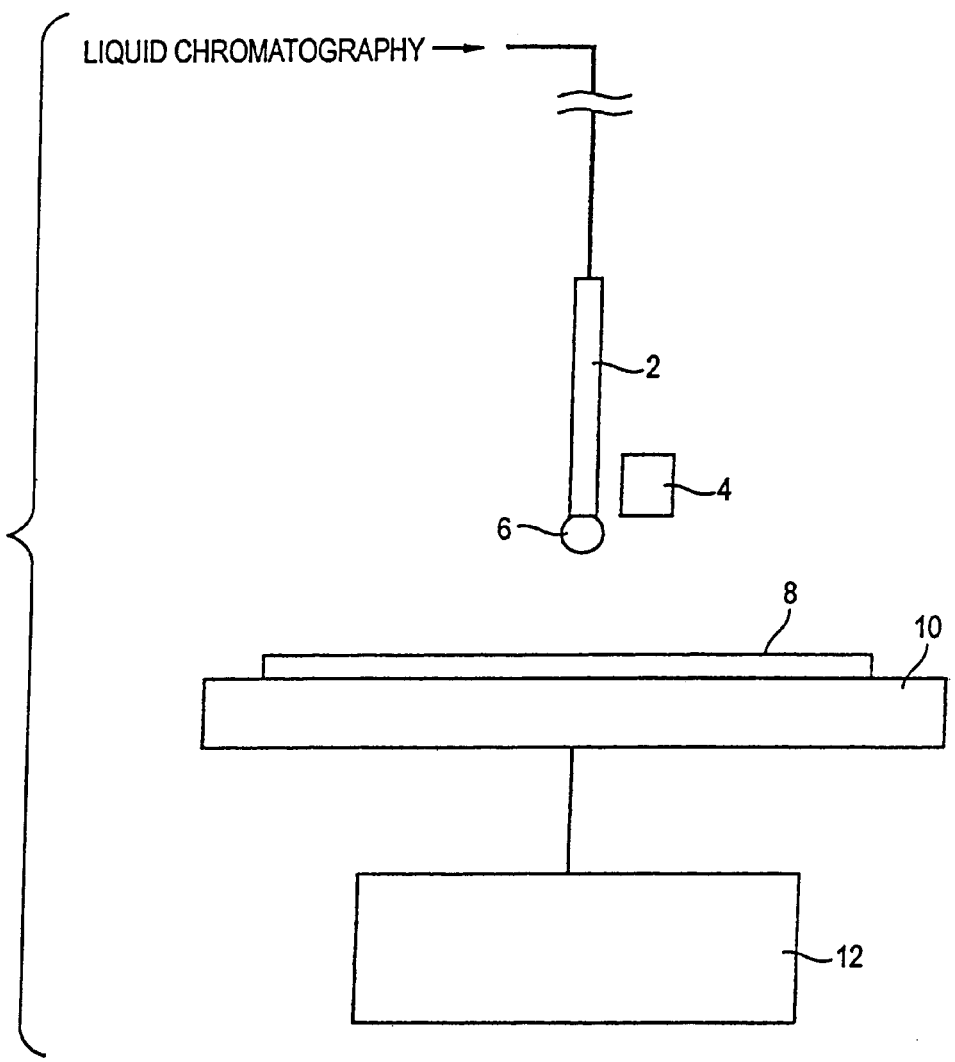
FIG. 1 is a schematic diagram showing the constitution of a fractionating apparatus according to one embodiment of the invention.

FIG. 1 is a schematic diagram showing the constitution of a fractionating apparatus according to one embodiment of the invention.

The fractionating apparatus according to this embodiment comprises a probe 2, a proximity sensor 4, a sample plate 8 for MALDI-TOF, a stage 10, and a control unit 12. The probe 2 drops a liquid droplet 6 from a high speed liquid chromatography on the sample plate. The proximity sensor 4 is disposed sideways of a distal end portion of the probe 2, as a distance measuring unit for measuring a distance between a distal end of the probe 2 and the sample plate 8. The sample plate 8 collects the liquid droplet 6 dropped from the probe 2. The stage 10 moves the sample plate 8 mounted thereon in a vertical direction and a in-plane direction. The control unit 12 controls a movement of the stage 10. The stage 10 and the control unit 12 constitute a support mechanism.

The proximity sensor 4 may be an ultrasonic sensor or an eddy current sensor, for example. In the mass analysis with MALDI-TOF, because the needed amount of sample solution is as small as 1 μL or less in most cases, the detection distance of the proximity sensor 4 is about 1 to 1.5 mm.

The sample plate 8 is mounted on the stage 10, and moved in the vertical direction and the in-plane direction. Usually, the sample plate 8 has defined the drop positions as many as 192 or 384, for example, in which a liquid droplet 6 containing sample constituents is dropped from the probe 2 to each of the drop positions.

The control unit 12 controls the movement of the stage 10 in accordance with the following two ways.

(1) in-plane control for positioning the stage so that the liquid droplet may be dropped correctly at a predetermined drop position on the sample plate 8 by moving the stage 10 on the horizontal plane, and (2) vertical control for controlling the movement of the stage 10 so that the liquid droplet 6 produced at the distal end of the probe 2 may contact with the drop position of the sample plate 8 by making the sample plate 8 closer to the probe 2 when dropping the liquid droplet.

The in-plane control of (1) involves positioning the stage 10 according to a preset division schedule.

The vertical control of (2) involves deciding the movement amount of the stage 10 based on the size (drop amount) of the liquid droplet 6 produced at the distal end of the probe 2. For example, if the size of liquid droplet 6 is 100 nL, its diameter is about 0.6 mm, assuming that the shape of liquid droplet 6 is spherical. To contact the liquid droplet 6 with the sample plate 8, the distance between the distal end of the probe 2 and the sample plate 8 may be 0.6 mm. Thus, the control unit 12 involves measuring the distance between the distal end of the probe 2 and the sample plate 8 with the proximity sensor 4 and making the feedback control for the stage 10 based on the measured result.

The flow rate of effluent solution fed from the liquid chromatography is a fixed amount of about 1 μL/min. For example, when the division is made under the conditions where the flow rate of effluent solution from the liquid chromatography is 400 nL/min, and the drop amount of liquid droplet from the probe 2 is 100 nL, the liquid droplet is dropped from the probe 2 onto the sample plate 8 at every 15 seconds.

In the related art, the sample plate is fixed on the stage that can be moved vertically and horizontally, but the fixed plane is not completely horizontal, whereby the distance between the probe and the sample plate is not kept constant for whole surface of the sample plate. If both are made too closer, the probe contacts with the sample plate contact, and possibly hurts the sample plate. Also, if the distance between both is too large, the liquid droplet is out of contact with the sample plate, so that the amount of liquid droplet is changed, or the division is not allowed.

As in this invention, the proximity sensor 4 for measuring the distance between the probe 2 and the sample plate 8 is provided and the sample plate 8 is made closer to the probe 3 based on the measured result, so that the distance between the probe 2 and the sample plate 8 is kept constant at appropriate value.

The operation of this embodiment will be described below.

Figure 2:
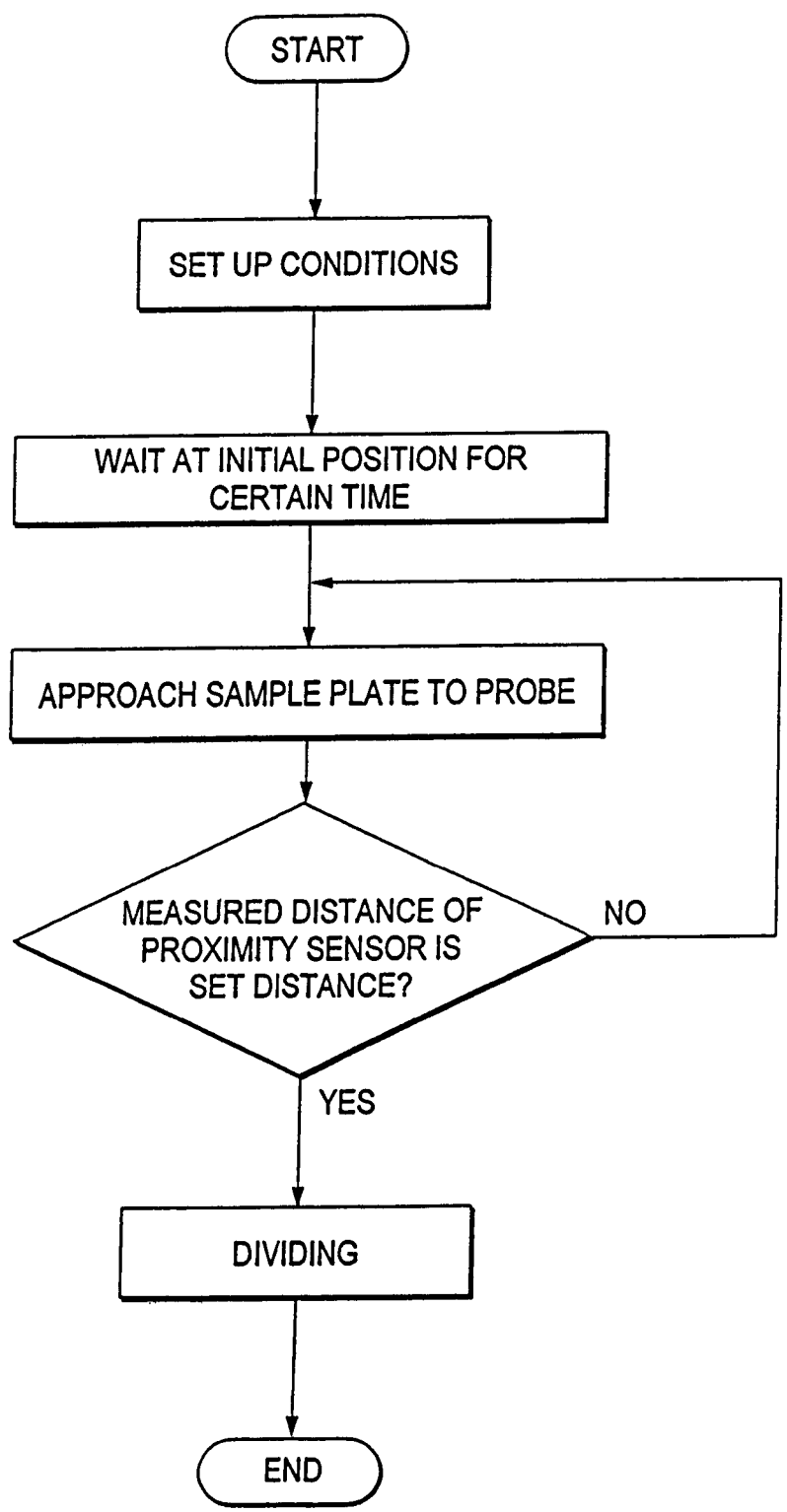
FIG. 2 is a flowchart showing the operation of the fractionating apparatus according to the embodiment of the invention.

FIG. 2 is a flowchart showing the operation of the embodiment.

In starting the division, the conditions such as the flow rate of effluent solution from the liquid chromatography, the drop amount of liquid droplet from the probe 2 and the detecting point (1 mm) of the proximity sensor 4 are input into the apparatus. The stage 10 with the sample plate 8 mounted waits at an initial position (e.g., distance to the probe 2 is 5 mm) for a certain time (e.g., 15 seconds) until a desired amount of liquid droplet accumulates at the distal end of the probe 2. After the elapse of the certain time, the sample plate 8 is moved upwards to approach the probe 2. When the distance between the probe 2 and the sample plate 8 is 1 mm, the proximity sensor 4 is activated to measure the distance between both. When the amount of liquid droplet is 100 nL, because its diameter is 0.6 mm, the control unit 12 makes the feedback control for the stage 10 so that the measured value of the proximity sensor 4 may be 0.6 mm, and further moves the stage 10 closer by 0.4 mm. Then, the liquid droplet 6 and the sample plate 8 are contacted, and the division is made on the sample plate 8.

If the division is ended at one fractionating position, the stage 10 returns to the initial position. The control unit 12 controls the positioning of the stage 10 to make the division at the next fractionating position on the sample plate 8, and waits for a certain time. By repeating this operation, the division is made successively at the fractionating positions on the sample plate.

The same effects may be obtained when the FT-IR sample plate is mounted instead of the MALDI-TOF sample plate 8.

The amount of liquid droplet to be dropped from the probe 2 may be changed at will.

Also, the operator may set up the detecting position of the proximity sensor 4 at will. Also, the initial position of the sample plate 8 may be changed at will.

The diameter of liquid droplet 6 may be calculated by the operator, or automatically calculated by the apparatus (e.g., control unit 12).

The distance between the distal end of the probe 2 and the sample plate 8 in dropping the liquid droplet on the sample plate 8 may be acquired by automatically calculating the diameter of liquid droplet from the drop amount of liquid droplet, and setting up the distance under the control of the control unit 12.

Also, the operator may variably set the distance to the control unit 12.

What is claimed is:

1. A fractionating apparatus in which a plurality of individual liquid droplets are dropped onto a plate, wherein each liquid droplet is dropped onto a different location on the plate at a different time, comprising:

a probe having a distal end from which each liquid droplet is dropped;

the plate for collecting the liquid droplets dropped from said probe;

a support mechanism for moving said plate or said probe at least vertically;

a distance measuring unit for measuring a distance from the probe distal end to said plate; and a control unit for controlling a movement of said support mechanism so that the distance between the distal end of said probe and said plate is equal to a preset distance, based on a measured result of said distance measuring unit, when dropping each liquid droplet from said probe, wherein the preset distance between the distal end of said probe and said plate is acquired by calculating a diameter of the liquid droplet from a drop amount of the liquid droplet.

2. The fractionating apparatus according to claim 1, wherein said control unit can variably set the distance between the distal end of said probe and said plate when dropping each liquid droplet from said probe.

3. The fractionating apparatus according to claim 2, wherein said probe is connected to a distal end of a capillary column through which an effluent solution from a liquid chromatograph is fed.

4. The fractionating apparatus according to claim 1, wherein said probe is connected to a distal end of a capillary column through which an effluent solution from a liquid chromatograph is fed.

5. The fractionating apparatus according to claim 1, wherein said plate is a sample plate for MALDI-TOF.

6. The fractionating apparatus according to claim 1, wherein said plate is a sample plate for FT-IR.

7. The fractionating apparatus according to claim 1, wherein said distance measuring unit comprises a proximity sensor.

8. The fractionating apparatus according to claim 7, wherein the proximity sensor is one of an ultrasonic sensor and an eddy current sensor.

9. The fractionating apparatus according to claim 1, wherein said plate is a sample plate defining a predetermined number of drop positions, each drop position being adapted to receive one of the plurality of liquid droplets.

* * * * *